(12) United States Patent
Thomas et al.

(10) Patent No.: US 10,973,977 B2
(45) Date of Patent: Apr. 13, 2021

(54) INFUSION DEVICE HAVING A PUSHER DEVICE

(71) Applicant: Fresenius Vial SAS, Brézins (FR)

(72) Inventors: Fabien Thomas, Saint Victor de Cessieu (FR); Rémy Wolff, Morette (FR); Eric Gitton, Four (FR); Denis Bertagnolio, Sillans (FR)

(73) Assignee: Fresenius Vial SAS, Brézins (FR)

( * ) Notice: Subject to any disclaimer, the term of this patent is extended or adjusted under 35 U.S.C. 154(b) by 344 days.

(21) Appl. No.: 16/061,482

(22) PCT Filed: Dec. 19, 2016

(86) PCT No.: PCT/EP2016/081735
§ 371 (c)(1),
(2) Date: Jun. 12, 2018

(87) PCT Pub. No.: WO2017/108686
PCT Pub. Date: Jun. 29, 2017

(65) Prior Publication Data
US 2020/0023121 A1    Jan. 23, 2020

(30) Foreign Application Priority Data

Dec. 21, 2015  (EP) .................................... 15307077

(51) Int. Cl.
*A61M 5/145*  (2006.01)
*A61M 5/142*  (2006.01)
(52) U.S. Cl.
CPC ........ *A61M 5/1456* (2013.01); *A61M 5/1458* (2013.01); *A61M 5/14236* (2013.01);
(Continued)
(58) Field of Classification Search
CPC .. A61M 5/145; A61M 5/1456; A61M 5/1458; A61M 2005/14573
See application file for complete search history.

(56) References Cited

U.S. PATENT DOCUMENTS

| | | |
|---|---|---|
| 4,544,369 A | 10/1985 | Skakoon et al. |
| 4,976,696 A | 12/1990 | Sanderson et al. |

(Continued)

FOREIGN PATENT DOCUMENTS

| | | |
|---|---|---|
| CN | 201692438 | 1/2011 |
| DE | 10235468 | 4/2003 |
| EP | 0916353 A1 | 5/1999 |

OTHER PUBLICATIONS

International Search Report and Written Opinion, counterpart International Appl. No. PCT/EP2016/081735, dated Mar. 17, 2017 (12 pages).

(Continued)

*Primary Examiner* — Laura A Bouchelle
(74) *Attorney, Agent, or Firm* — Cook Alex Ltd.

(57) ABSTRACT

An infusion device (3) for administering a medical fluid to a patient, comprises a housing (30) and a receptacle (300) arranged on the housing (30) for receiving a syringe (4), the syringe (4) having a barrel (41) for containing a medical fluid and a plunger (42) movable relative to the barrel (41) for delivering the medical fluid out of the barrel (41). A pusher device (32) is movable relative to the housing (30) for acting onto the plunger (42) for moving the plunger (42) relative to the barrel (41), and a drive mechanism (38) drives the pusher device (32). A coupling mechanism (36, 37) is operative to couple the plunger (42) to the pusher device (32) or to couple the pusher device (32) to the drive mechanism (38), and an actuation mechanism arranged on the pusher device (32) comprises an actuation element (33) for actuating the coupling mechanism (36, 37) between a coupling state and an uncoupling state. Herein, the actuation mechanism comprises a first threaded element (34) rotatable about a rotational axis (342) and a second threaded element (331) movable along the first threaded element (34), the second threaded element (331) being in threaded engage- (Continued)

ment with the first threaded element (34) such that the first threaded element (34) is rotated when the second threaded element (331) is moved along the first threaded element (34), wherein the actuation element (33) is actuatable to move the second threaded element (331) along the first threaded element (34), the first threaded element (34) being operatively connected to the coupling mechanism (36, 37). In this way an infusion device is provided which in an easy and comfortable manner allows a user to actuate a coupling mechanism, in particular for installing a syringe on a receptacle of the infusion device.

13 Claims, 5 Drawing Sheets

(52) U.S. Cl.
CPC ............. *A61M 2005/14506* (2013.01); *A61M 2005/14533* (2013.01)

(56) References Cited

U.S. PATENT DOCUMENTS

| | | |
|---|---|---|
| 6,423,035 B1 | 7/2002 | Das et al. |
| 6,551,277 B1 * | 4/2003 | Ford .................. A61M 5/1456 340/540 |
| 2010/0063447 A1 | 3/2010 | Stempfle et al. |

OTHER PUBLICATIONS

Search Report, counterpart Chinese App. No. 201680075333.8 (dated Jul. 20, 2020) (2 pages).

First Office Action with English translation, counterpart Chinese App. No. 201680075333.8 (dated Jul. 31, 2020) (20 pages).

* cited by examiner

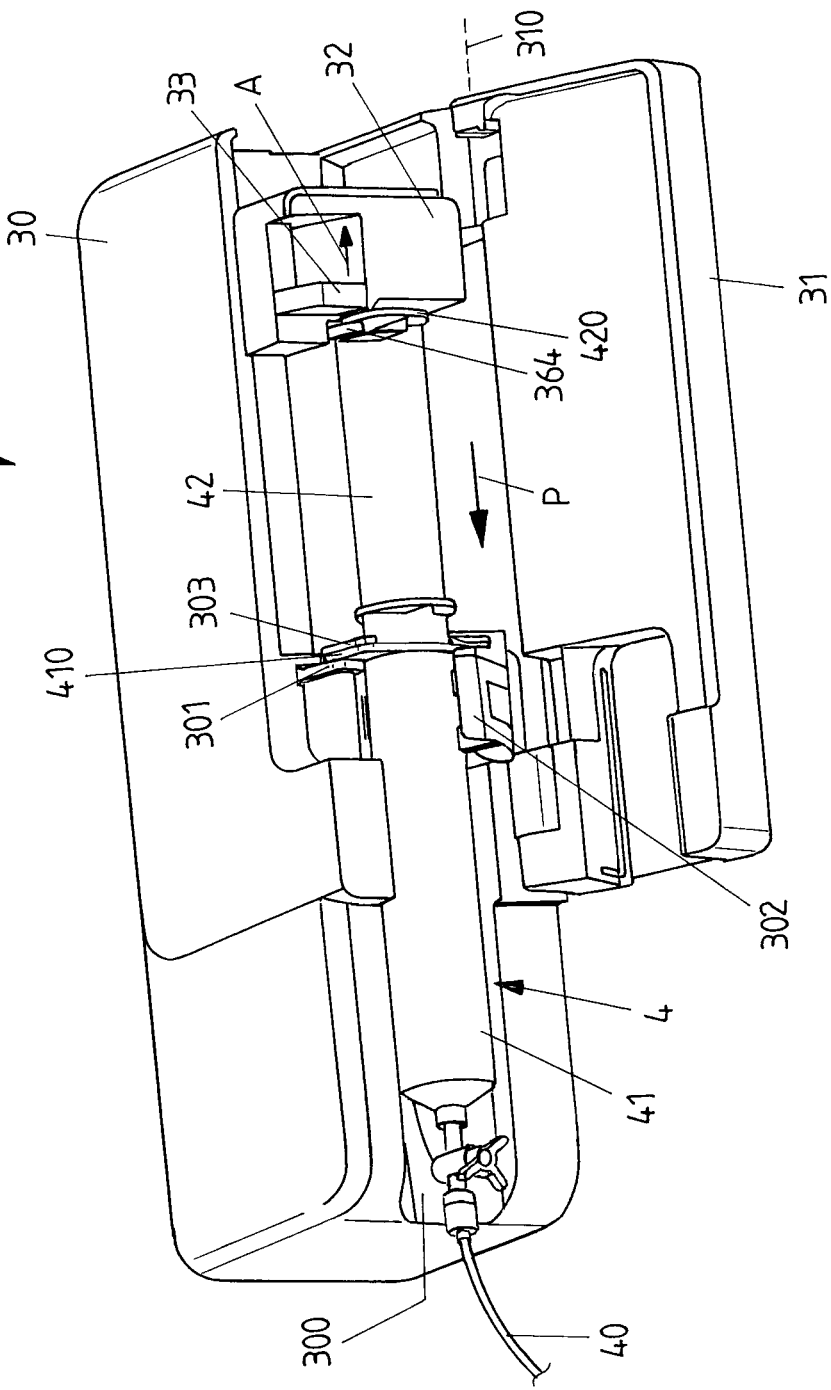

INFUSION DEVICE HAVING A PUSHER DEVICE

The present application is a U.S. National Stage of PCT International Patent Application No. PCT/EP2016/081735, filed Dec. 19, 2016, which claims priority to EP Application No. 15307077, filed Dec. 21, 2015, both of which are hereby incorporated herein by reference:

The invention relates to an infusion device for administering a medical fluid to a patient according to the preamble of claim 1.

An infusion device of this kind comprises a housing and a receptacle arranged on the housing for receiving a syringe. The syringe comprises a barrel for containing a medical fluid and a plunger movable relative to the barrel for delivering the medical fluid out of the barrel via an infusion line towards the patient. Herein, a pusher device is movable relative to the housing for moving the plunger relative to the barrel, the pusher device being driven by a drive mechanism such that during an infusion operation the medical fluid can be delivered from the barrel to the patient in a controlled fashion at a set infusion rate.

To set up an infusion procedure, a syringe is manually installed on the receptacle of the infusion device, and the pusher device is brought into operative connection with the plunger in order to enable the pusher device to push the plunger into the barrel for delivering the medical fluid from the barrel towards the patient. For installing the syringe on the receptacle, typically the pusher device is uncoupled from the drive mechanism such that the pusher device can freely be moved relative to the drive mechanism and in particular can be brought into engagement with the plunger for acting onto the plunger during an infusion operation. For the infusion operation, then, the pusher device is again coupled to the drive mechanism such that the drive mechanism can act onto the pusher device for moving the pusher device relative to the housing.

For coupling the drive mechanism with the pusher device, a coupling mechanism may be provided. The coupling mechanism, in a coupling state, establishes a coupling between the drive mechanism and the pusher device such that the pusher device can be driven by the drive mechanism and, in an uncoupling state, uncouples the drive mechanism from the pusher device such that the pusher device can freely be moved independent of the drive mechanism.

For actuating the coupling mechanism, an actuation mechanism is arranged on the pusher device, the actuation mechanism comprising an actuation element for actuating the coupling mechanism between the coupling state and the uncoupling state.

Another coupling mechanism may be provided which is used to couple the plunger to the pusher device such that, during an infusion operation, the plunger cannot be moved independently of the pusher device.

For example in a hospital environment, in particular in an intensive care unit of a hospital, a rather large number of infusion devices are arranged at the bedside of a patient. In modern systems herein infusion devices are arranged in a vertical column on one or multiple racks and are placed on a stand or the like in order to organize the infusion devices at the bedside of the patient. The more infusion devices herein are arranged in a stack, the smaller the available room for the individual infusion devices is and the more important it is that a user can conveniently access the individual infusion devices.

With such constraints it is desirable to provide an actuation mechanism which allows a user to actuate a coupling mechanism in an easy and comfortable way. The actuation of the coupling mechanism herein takes place for example during the set-up of an infusion procedure in order to manually install a syringe on an infusion device, for which first the pusher device must be uncoupled from the drive mechanism by actuating a suitable coupling mechanism and, after the syringe has been installed on the infusion device, the coupling must once more be established in order to move the pusher device together with the plunger to deliver a medical fluid from the barrel.

From EP 0 916 353 B1 an infusion device in the shape of a syringe pump is known, in which a button acting onto a lever is arranged on a pusher device for actuating a coupling mechanism between a coupling state and an uncoupling state.

It is an object of the instant invention to provide an infusion device which in an easy and comfortable manner allows a user to actuate a coupling mechanism, in particular for installing a syringe on a receptacle of the infusion device.

This object is achieved with an infusion device comprising the features of claim 1.

Herein, the actuation mechanism comprises a first threaded element rotatable about a rotational axis and a second threaded element movable along the first threaded element, the second threaded element being in threaded engagement with the first threaded element such that the first threaded element is rotated when the second threaded element is moved along the first threaded element, wherein the actuation element is actuatable to move the second threaded element along the first threaded element, the first threaded element being operatively connected to the coupling mechanism.

Accordingly, the actuation element acts onto a second threaded element and moves the second threaded element longitudinally relative to a first threaded element. A longitudinal movement of one element hence is transferred into a rotational movement of the other element. The first threaded element herein is connected to the coupling mechanism via a suitable gearing, such that the rotational movement of the first threaded element is transferred to the coupling mechanism to move the coupling mechanism from its coupled state to the uncoupled state or vice versa.

The first threaded element may for example be a high helix screw, whereas the second threaded element for example is a high helix nut. The threaded engagement between the high helix screw and the high helix nut is beneficially defined by a rather steep pitch angle, thus having a rather large pitch such that the lateral movement of the high helix nut along the high helix screw is translated with low force to the rotational movement of the high helix screw. In particular, the pitch angle must be larger than the friction coefficient such that a lateral movement of the high helix nut with respect to the high helix screw is possible and leads to a translation into a rotation of the high helix screw.

The actuation direction of the second threaded element relative to the first threaded element, in one embodiment, is directed in parallel to a pushing direction along which the pusher device is movable relative to the housing. The pushing direction generally may for example be oriented along a horizontal direction, the actuation direction of the second threaded element hence also being oriented horizontally. If the actuation element is for example arranged on the pusher device on a front face of the infusion device, a user may easily access the actuation element and may move it horizontally in order to move the second threaded element relative to the first threaded element and thus to actuate the coupling mechanism. Because the actuation direction in this way may be oriented horizontally, no up- and downward movement of the actuation element is required, making it possible to comfortably actuate said actuation element even on an infusion device having a fairly low height.

The actuation element may for example be a lever which is pivotable about a pivot axis relative to the pusher device. Herein, the second threaded element is carried along with the actuation element when the actuation element is pivoted, the second threaded element performing a (pure) longitudinal movement along the first threaded element in order to rotate the first threaded element about its rotational axis.

In one embodiment, the first threaded element carries a first gear wheel. The first gear wheel is fixedly connected to the first threaded element and is rotated together with the first threaded element when the first threaded element is rotated by moving the second threaded element along the first threaded element.

The first gear wheel may have an outer circumferential toothing via which it is in engagement with a second gear wheel, the second gear wheel being rotated when the first gear wheel is rotated.

The second gear wheel may interact with a cam connected to a shaft, the cam being actuated for pivoting the shaft upon rotation of the second gear wheel. The shaft is coupled to the coupling mechanism such that by rotating the shaft the coupling mechanism is moved between its coupling state and its uncoupling state.

By means of the first gear wheel and the second gear wheel providing a gearing for transferring the rotational movement of the first threaded element to the shaft and via the shaft to the coupling mechanism a suitable reduction may be provided, thus allowing for a low force actuation of the actuation element for actuating the coupling mechanism.

In one embodiment, the second gear wheel may be constituted to interact with a first cam connected to a first shaft and to a second cam connected to a second shaft. When rotating the second gear wheel, both cams are actuated for pivoting the first shaft and the second shaft in order to actuate a first coupling mechanism and a second coupling mechanism.

Hence, via the second gear wheel an actuation movement may be transferred to multiple coupling mechanisms, a first coupling mechanism for example being operative to couple the pusher device to the plunger, and a second coupling mechanism being operative to couple the pusher device to the drive mechanism. Hence, from the gear wheel an actuation movement is transferred to multiple coupling mechanisms, such that multiple coupling mechanisms can be actuated together (synchronously or with a slight relative delay) by acting onto the actuation element of the actuation mechanism.

The second coupling mechanism is operative to couple the pusher device to the drive mechanism. In its coupling state the second coupling mechanism hence provides for a coupling between the drive mechanism and the pusher device such that the pusher device can electrically be driven by means of the drive mechanism during an infusion operation. In its uncoupling state, in turn, the pusher device can freely be moved relative to the drive mechanism.

The first coupling mechanism serves to provide for a coupling between the pusher device and the plunger of the syringe such that, in particular, the plunger cannot be moved in the pushing direction independent of the pusher device during an infusion operation. For this, the first coupling mechanism may for example comprise a coupling element pivotably arranged on the pusher device. The coupling element can be pivoted with respect to the pusher device such that it engages with a flange of the plunger in a coupling state and can be disengage from the flange for releasing the plunger from the pusher device.

The idea underlying the invention shall subsequently be described in more detail with respect to the embodiments described in the figures. Herein:

FIG. 3 shows a schematic view of an infusion device;

Figure 1:
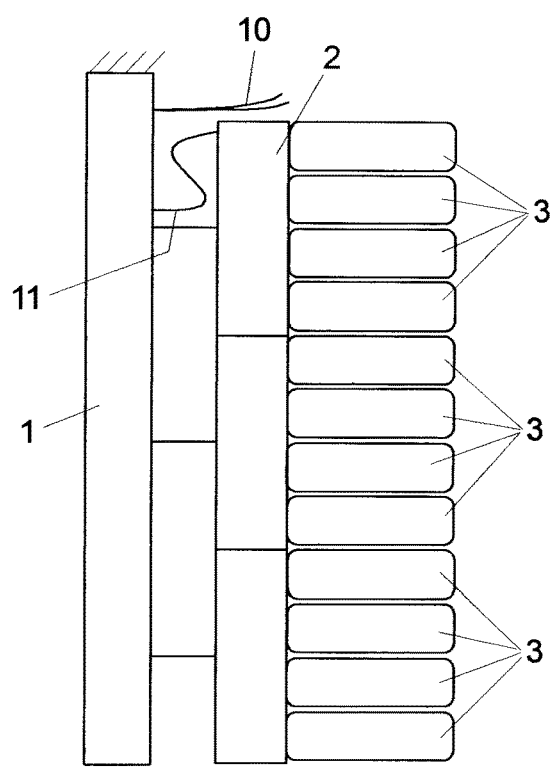
FIG. 1 shows a schematic view of multiple infusion devices arranged on one or multiple racks.

FIG. 1 shows in a schematic drawing an arrangement of infusion devices 3 on one or multiple racks 2. The infusion devices 3 may for example be constituted as syringe pumps or as volumetric (peristaltic) infusion devices and generally serve to administer medical fluids to a patient for example in a hospital environment, for example in an intensive care unit of a hospital. The infusion devices 3 herein are organized to form a vertical stack on the rack 2 and, via the rack 2, are connected to a holding device 1 which for example is connected to the ceiling of the patient's bedroom.

The rack 2 serves as a communication link as well as a power supply for the infusion devices 3. For this, connection lines 10, 11 constituting a power supply line as well as one or multiple communication lines are connected to the rack 2, the rack 2 providing for a data connection as well as for a power connection for the infusion devices 3 arranged on the rack 2.

Figure 2:
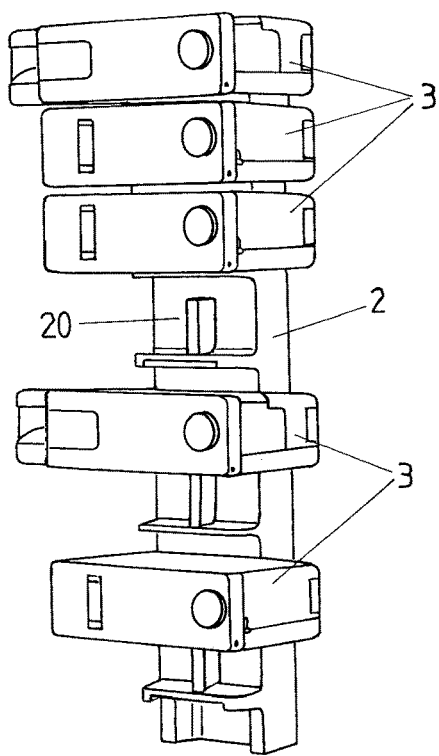
FIG. 2 shows another view of infusion devices arranged on a rack.

Another view of infusion devices 3 arranged on receptacles 20 of a rack 2 is shown in FIG. 2. The infusion devices 3, as said, generally may be constituted as syringe pumps or as volumetric (peristaltic) infusion pumps.

It is a desire to arrange a large number of infusion devices 3, for example up to 24 infusion devices, at the bedside of a patient in order to be able to infuse a multiplicity of different medical solutions to the patient, such medical solutions including drugs, nutritional solutions, saline solutions or the like. Since the infusion devices 3 generally are arranged in a vertical stack on one or multiple racks 2, in order to be able to increase the number of infusion devices 3 on rack 2 it is required to reduce the height of the infusion devices 3, assuming that a maximum height of a rack 2 should not be exceeded to allow a convenient access to all infusion devices 3 placed on the rack 2. This however comes with the drawback that the vertical space per infusion device 3 is reduced, thus reducing the available space a user has to access an individual infusion device 3.

FIG. 3 shows a view of a single infusion device 3 in the shape of a syringe pump, the infusion device 3 having a housing 30. On the front face of the housing 30 a receptacle 300 for receiving a syringe 4 is formed. A door 31 is pivotable about a pivot axis 310 with respect to the housing 30, wherein the door 31 can be opened to access the receptacle 300 in order to place a syringe 4 on the receptacle 300 on to remove the syringe 4 from the receptacle 300 and can be closed to perform an infusion operation.

The syringe 4 comprises a barrel 41 and a plunger 42 movable relative to the barrel 41. The barrel 41 contains a medical solution to be delivered to the patient, the plunger 42 being pushable into the barrel 41 in order to deliver a medical solution from the barrel 41 via an infusion line 40 connected to the barrel 41 to the patient.

The infusion device 3 comprises a pusher device 32 being movable along a pushing direction P relative to the housing 30 and being constituted to act onto the plunger 42 in order to move the plunger 42 into the barrel 41. The pusher device 32 is connected to a drive mechanism such that the pusher device 32 during operation of the infusion device 3 can electrically be pushed in the pushing direction P to move the plunger 42 into the barrel 41 in order to infuse the medical solution from the barrel 41 to the patient at for example a constant dose rate.

To prepare the infusion device 3 for an infusion operation, the barrel 41 is arranged on the receptacle 300 such that a flange 410 of the barrel 41 comes to rest in between stops 301, 303 of the housing 30. In this way the barrel 41 is axially held in position along the pushing direction P with respect to the housing 30, and by pivoting a barrel holder 302 in the shape of a clamp towards the barrel 41 the barrel 41 is fixed on the receptacle 300.

When installing the syringe 4 on the infusion device 3, the pusher device 32 must be brought into abutment with a flange 420 at an end of the plunger 42 remote from the barrel 41. For this, the pusher device 32 can be unclutched from the drive mechanism, as shall be explained in detail below, and can be freely moved along the pushing direction P relative to the housing 30 such that it can be brought into abutment with the plunger 42. After the pusher device 32 has been moved towards the plunger 42, a coupling element 364 (also denoted as antisiphon arm) can be pivoted with respect to the pusher device 32 and can be made to engage with the flange 420 such that the plunger 42 is secured relative to the pusher device 32 and in particular cannot be moved in the pushing direction P independent of the pusher device 32.

To establish the coupling of the pusher device 32 with the plunger 42 a first coupling mechanism 36 is provided, and to establish the coupling of the pusher device 32 to the drive mechanism a second coupling mechanism 37 is provided, as is shown in FIGS. 4A, 4B and 5A, 5B. The coupling mechanisms 36, 37 can be actuated via a common actuation element 33 accessible from the front of the infusion device 3 and being placed on the pusher device 32, as visible in FIG. 3.

To actuate the coupling mechanisms 36, 37, a common actuation mechanism is used which is substantially enclosed in the pusher device 32 and during operation of the infusion device 3 is moved along with the pusher device 32. Herein, the actuation element 33 is constituted as a lever which is, via a lever arm 330, pivotable about a pivot axis 332 relative to the pusher device 32. In particular, for transferring the coupling mechanisms 36, 37 into an uncoupling state (in which the first coupling mechanism 36 does not couple the plunger 42 to the pusher device 32 and the second coupling mechanism 37 uncouples the pusher device 32 from the drive mechanism) the actuation element 33 is actuated in an actuation direction A and hence is pivoted with respect to the pusher device 32. The pivot axis 332 herein is locationally fixed on the pusher device 32, such that the actuation element 33 is actuated with respect to the pusher device 32, but during operation of the infusion device 3 is moved together with the pusher device 32.

As the actuation element 33 is actuated in the actuation direction A, the lever arm 330, which is coupled with a threaded element 331 in the shape of a high helix nut, carries the threaded element 331 along and moves it longitudinally along another threaded element 34 in the shape of a high helix screw having an outer screw thread via which the threaded element 331 in the shape of the high helix nut engages with the threaded element 34 in the shape of the high helix screw. As the threaded element 331 in the shape of the high helix nut is moved along the threaded element 34 in the shape of the high helix screw, the threaded element 34 in the shape of the high helix screw is rotated about its longitudinal axis 342, thus rotating a gear wheel 341 at a far end of the threaded element 34 in the shape of the high helix screw.

The gear wheel 341, with an outer circumferential toothing, engages with a toothing of another gear wheel 35 and hence, when rotated, rotates the gear wheel 35 about its rotational axis 354. The gear wheel 35 in turn engages with a first cam 362 of the first coupling mechanism 36 and with a second cam 372 of the second coupling mechanism 37. The first cam 362 herein is connected to a shaft 361, and the second cam 372 is connected to a shaft 370, the shafts 361, 370 being pivoted about their longitudinal axes 360, 371 upon actuation by the gear wheel 35.

The first cam 362 engages via a pin 363 with an engagement contour 353 on a side of the gear wheel 35 facing the first cam 362, such that upon rotation of the gear wheel 35 the cam 362 is pivoted.

The second cam 372 in turn engages with cam 352 on the outer circumference of the gear wheel 35, such that the cam 372 is pivoted upon rotation of the gear wheel 35.

Figure 4A:
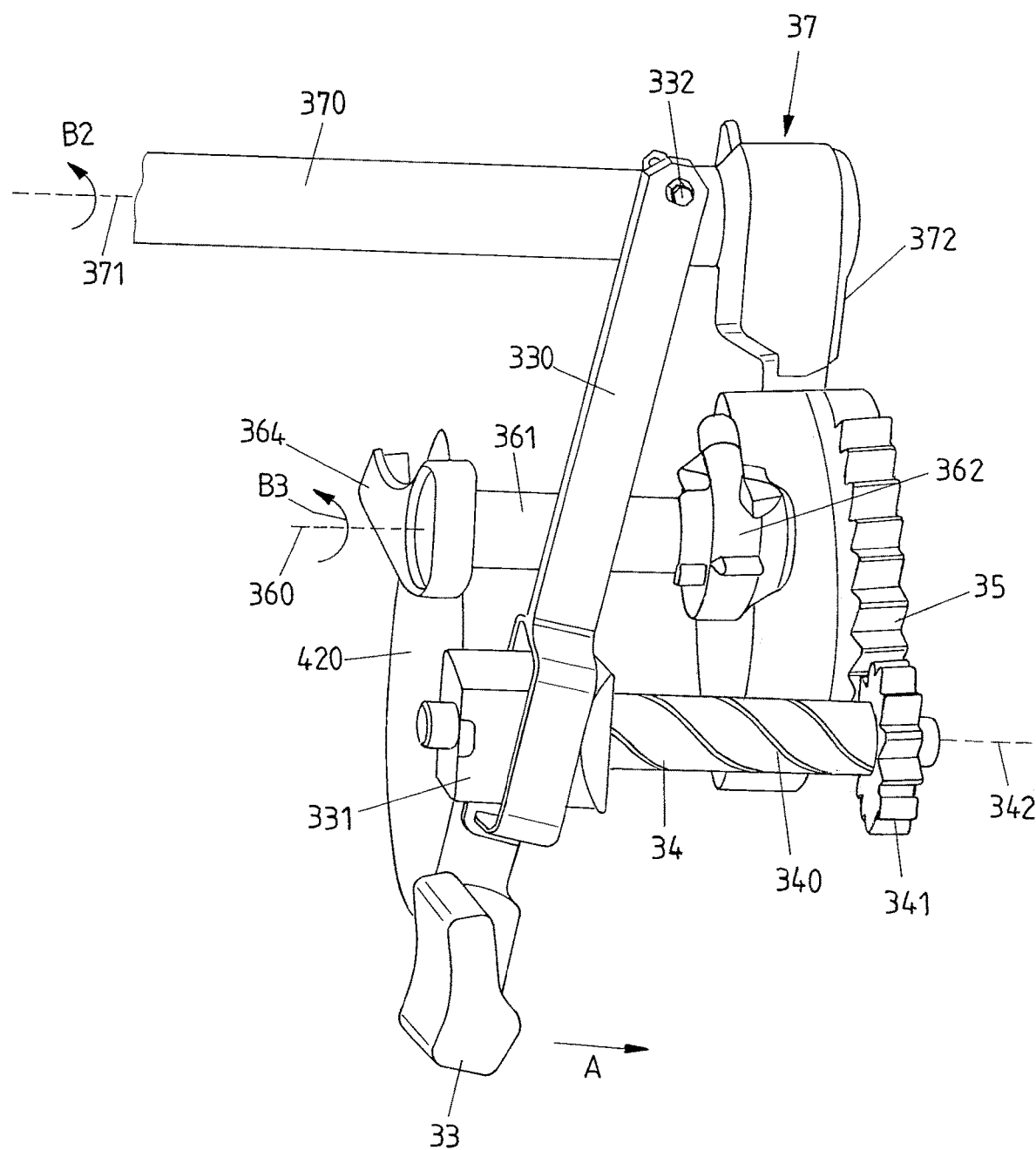
FIG. 4A shows a view of an actuation mechanism for actuating a coupling mechanism.
Figure 4B:
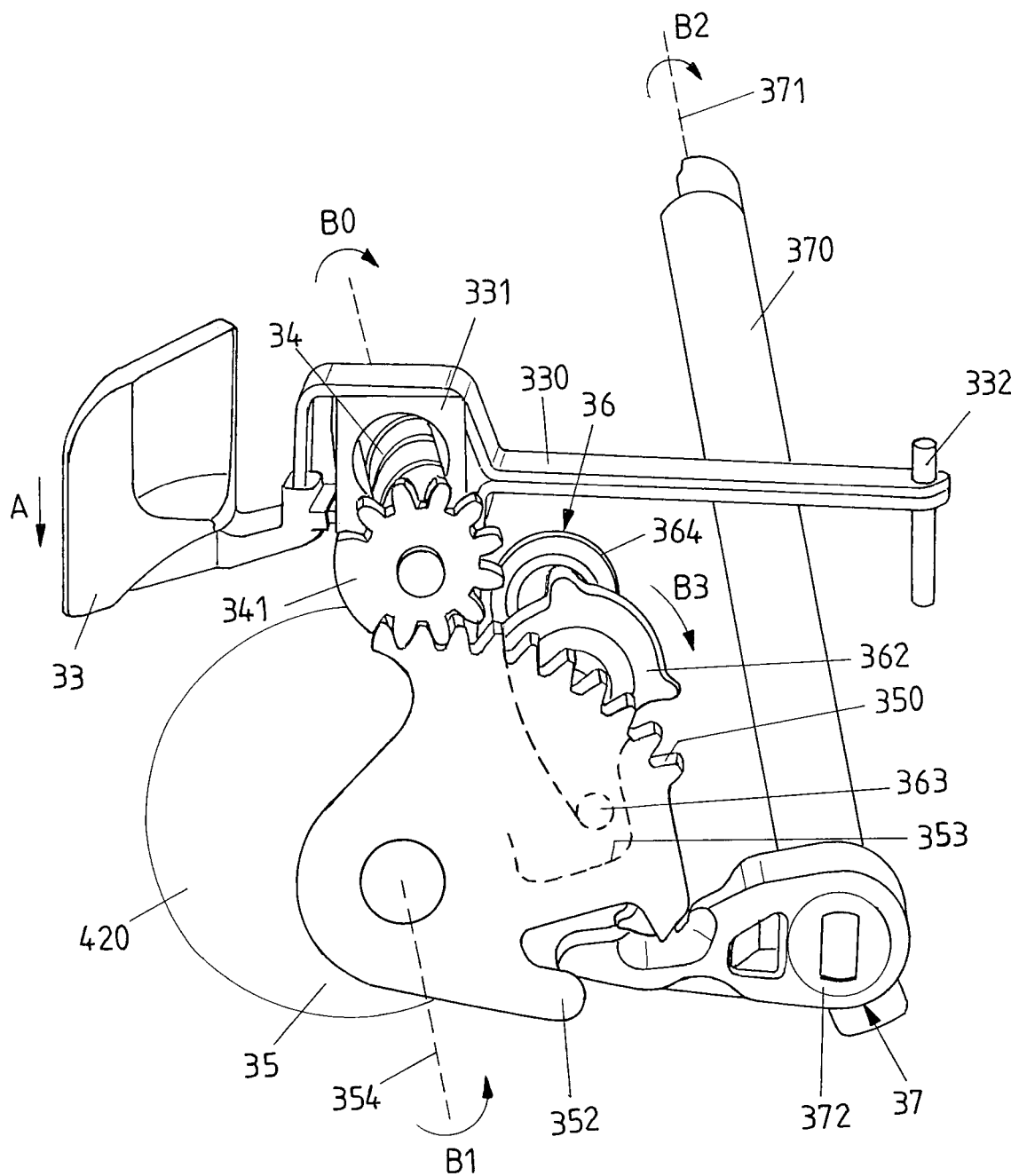
FIG. 4B shows another view of the arrangement of FIG. 4A.

In particular, as the actuation element 33 is actuated in the actuation direction A, the threaded element 34 in the shape of the high helix screw is rotated in a rotational direction B0 as shown in FIG. 4B. This rotates the gear wheel 341 and causes a rotation of the gear wheel 35 in the rotational direction B1, which pivots the first cam 362 in the direction B3 and the second cam 372 in the direction B2.

By means of the engagement of the threaded element 331 in the shape of the high helix nut and the threaded element 34 in the shape of the high helix screw, hence, a longitudinal movement (of the threaded element 331) is translated into a rotational movement (of the threaded element 34), which is transferred to the coupling mechanisms 36, 37 for moving the coupling mechanisms 36, 37 between their coupling state and their uncoupling state.

The first cam 362, via the shaft 361, is connected to the coupling element 364 such that, when actuating the first cam 362 by means of the gear wheel 35, the coupling element 364 can be moved relative to the pusher device 32 to couple the plunger 42 to the pusher device 32 or to uncouple the plunger 42 from the pusher device 32.

When actuating the coupling mechanism 36, in fact two movements take place. On the one hand, the coupling element 364 is rotated as described above. In addition, the coupling element 364 (together with the shaft 361) is translated along the rotational axis 360, due to the geometry of the engagement contour 353 formed on the gear wheel 35. The translational movement herein is such that, when transferring the coupling mechanism from the uncoupling state into the coupling state, the coupling element 364 is rotated towards the plunger 42 and at the same time is moved to approach the pusher device 32 such that the plunger flange 420 is caught in between the coupling element 364 and the pusher device 32. When transferring the coupling mechanism 36 from the coupling state to the uncoupling state (by pushing the actuation element 33 in the actuation direction A) an opposite movement takes place, i.e. the coupling element 364 is rotated away from the plunger 42 and at the same time is translationally moved away from the pusher device 32 to give room to release the plunger flange 420 from the pusher device 32.

Figure 5A:
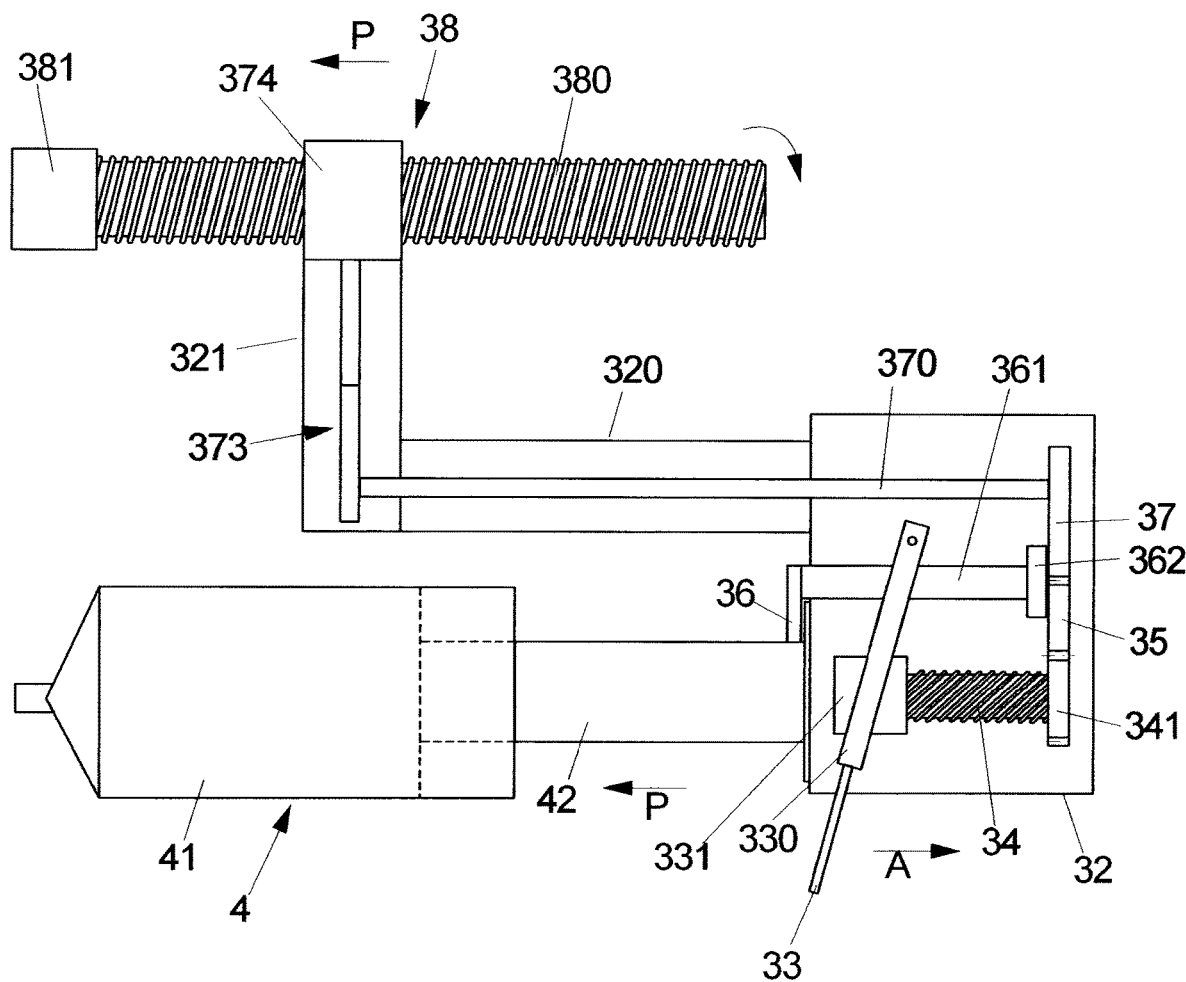
FIG. 5A shows a schematic view of the pusher device in connection with a drive mechanism for driving the pusher device.
Figure 5B:
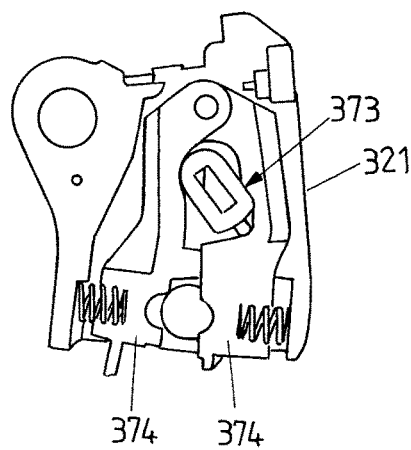
FIG. 5B shows a schematic view of a coupling mechanism for coupling the pusher device to the drive mechanism.

The second cam 372, via the shaft 370, is connected to an actuation system 373 and via the actuation system 373 to coupling elements 374 in the shape of half nuts, as schematically is shown in FIGS. 5A and 5B. The half nuts are pivotably arranged on a drive element 321 and serve to engage with a spindle 380 of the drive mechanism 38 schematically illustrated in FIG. 5A. When engaged with the spindle 380, a threaded engagement between the spindle 380 and the half nuts 374 is established, such that a rotational movement of the spindle 380 causes the drive element 321 to longitudinally move along the spindle 380, thus driving the pusher device 32. For this, the spindle 380 is operatively connected to a drive motor 381, and the drive element 321 is connected via an arm 320 to the pusher device 32.

By rotating the shaft 370 when actuating the second cam 372, the half nuts 374 can be moved between their coupled and their uncoupled position. In particular, when actuating the actuation element 33 in the actuation direction A, the second cam 372 is pivoted and hence moves the shaft 370 to move the half nuts 374 to their uncoupled position (FIG. 5B) such that the pusher device 32 is uncoupled from the drive mechanism 38. When uncoupled, the pusher device 32 can freely be moved with respect to the drive mechanism 38, such that a syringe 4 may be installed on the infusion device 3, or a syringe 4 may be uninstalled from the infusion device 3.

The actuation of the coupling mechanisms 36, 37 takes place together (synchronously or with a slight relative delay) by actuating the actuation element 33, wherein the actuation direction A extends in parallel to the pushing direction P along which the pusher device 32 is movable. The actuation element 33 hence is actuated along a horizontal direction, which makes the actuation mechanism suitable also for infusion devices 3 having a low height.

When an actuation has taken place (by actuating the actuation element 33 in the actuation direction A) and the actuation element 33 is again released, it can be provided that the actuation element 33 and together with it the coupling mechanisms 36, 37 are automatically reverted to their initial, coupling state. For this, the coupling mechanisms may each comprise a spring element for mechanically pretensioning the coupling mechanisms 36, 37 towards their coupling state (FIG. 4A). Such spring elements (not shown in the figures) may for example act onto the shafts 361, 370 of the coupling mechanisms 36, 37. In addition, a spring element may act for example onto the gear wheel 35 to provide a tensioning force towards the initial, non-actuated state.

By means of the actuation mechanism with its threaded elements 331, 34, a translational movement is transferred into a rotational movement. The actuation mechanism can generally be actuated with low force, hence being comfortable to use for a user.

The invention is not limited to the embodiments described above, but generally may be used also on entirely different infusion devices.

An actuation mechanism of the kind described above can be used also to actuate only a single coupling mechanism, wherein it may be beneficial to use the actuation mechanism to actuate multiple coupling mechanisms at the same time.

In combination with the threaded elements used to translate the longitudinal movement into the rotational movement, in principle any suitable gearing can be used to transfer the movement to an associated coupling mechanism.

LIST OF REFERENCE NUMERALS

1 Holding device
10, 11 Connection line
2 Rack arrangement
20 Receptacle
3 Infusion device
30 Housing
300 Receptacle
301, 303 Stop
302 Barrel holder
31 Door
310 Pivot axis
32 Pusher device
320 Arm
321 Drive element
33 Actuation element
330 Lever arm
331 High helix nut
332 Pivot axis
34 High helix screw
340 Screw thread
341 Gear wheel
342 Rotational axis
35 Gear wheel
350 Toothing
351,352 Cam
353 Engagement contour
354 Rotational axis
36 Coupling mechanism
360 Rotational axis
361 Shaft
362 Cam
363 Pin
364 Coupling element (antisiphon arm)
37 Coupling mechanism
370 Shaft
371 Rotational axis
372 Cam
373 Gearing
374 Half nuts
38 Drive mechanism
380 Spindle
381 Drive device (electric motor)
4 Syringe
40 Infusion line
41 Barrel (cylindrical tube)
410 Flange
42 Plunger
420 Flange
A Actuation direction
B0, B, B2, B3 Rotational movement
P Pushing direction

The invention claimed is:
1. An infusion device for administering a medical fluid to a patient, comprising:
    a housing,
    a receptacle arranged on the housing for receiving a syringe, the syringe having a barrel for containing a medical fluid and a plunger movable relative to the barrel for delivering the medical fluid out of the barrel, a pusher device movable relative to the housing for acting onto the plunger for moving the plunger relative to the barrel, a drive mechanism for driving the pusher device, at least one coupling mechanism operative to couple the plunger to the pusher device or to couple the pusher device to the drive mechanism, and an actuation mechanism arranged on the pusher device and comprising an actuation element for actuating the at least one coupling mechanism between a coupling state and an uncoupling state, wherein the actuation mechanism comprises a first threaded element rotatable about a rotational axis and a second threaded element movable along the first threaded element, the second threaded element being in threaded engagement with the first threaded element and configured to rotate the first threaded element when the second threaded element is moved along the first threaded element, wherein the actuation element is configured to move the second threaded element along the first threaded element, the first threaded element being operatively connected to the at least one coupling mechanism.

2. The infusion device according to claim 1, wherein the first threaded element is a high helix screw.

3. The infusion device according to claim 1, wherein the second threaded element is a high helix nut.

4. The infusion device according to claim 1, wherein the second threaded element is movable relative to the first threaded element along an actuation direction extending in parallel to a pushing direction along which the pusher device is movable relative to the housing.

5. The infusion device according to claim 1, wherein the actuation element is constituted as a lever pivotable about a pivot axis relative to the pusher device, the second threaded element being carried along with the actuation element when the actuation element is pivoted.

6. The infusion device according to claim 1, wherein the first threaded element carries a first gear wheel rotatable together with the first threaded element.

7. The infusion device according to claim 6, wherein the first gear wheel is in engagement with a second gear wheel, the second gear wheel being rotated upon rotation of the first gear wheel.

8. The infusion device according to claim 7, wherein the second gear wheel interacts with a cam connected to a shaft, the cam being actuated for pivoting the shaft upon rotation of the second gear wheel.

9. The infusion device according to claim 7, wherein the at least one coupling mechanism comprises a first coupling mechanism and a second coupling mechanism, and the second gear wheel interacts with:

a first cam connected to a first shaft, the first cam being actuated for pivoting the first shaft upon rotation of the second gear wheel, wherein the first shaft is configured to actuate the first coupling mechanism, and a second cam connected to a second shaft, the second cam being actuated for pivoting the second shaft upon rotation of the second gear wheel, wherein the second shaft is configured to actuate the second coupling mechanism.

10. The infusion device according to claim 1, wherein the at least one coupling mechanism comprises:

a first coupling mechanism operative to couple the plunger to the pusher device, and a second coupling mechanism operative to couple the pusher device to the drive mechanism.

11. The infusion device according to claim 10, wherein the first coupling mechanism comprises a coupling element pivotably arranged on the pusher device.

12. An infusion device for administering a medical fluid to a patient, comprising:

a housing, a receptacle arranged on the housing for receiving a syringe, the syringe having a barrel for containing a medical fluid and a plunger movable relative to the barrel for delivering the medical fluid out of the barrel, a pusher device movable relative to the housing for acting onto the plunger for moving the plunger relative to the barrel, a drive mechanism for driving the pusher device, at least one coupling mechanism operative to couple the plunger to the pusher device or to couple the pusher device to the drive mechanism, and an actuation mechanism arranged on the pusher device and comprising an actuation means for actuating the at least one coupling mechanism between a coupling state and an uncoupling state, wherein the actuation mechanism comprises a first threaded means rotatable about a rotational axis and a second threaded means movable along the first threaded means, the second threaded means for threadedly engaging the first threaded means and for rotating the first threaded means as the second threaded means is moved along the first threaded means, the actuation means for means for moving the second threaded means along the first threaded means, the first threaded means being operatively connected to the at least one coupling mechanism.

13. A method of operating an infusion device for administering a medical fluid to a patient, the infusion device comprising:

a housing, a receptacle arranged on the housing for receiving a syringe, the syringe having a barrel for containing a medical fluid and a plunger movable relative to the barrel for delivering the medical fluid out of the barrel, a pusher device movable relative to the housing for acting onto the plunger for moving the plunger relative to the barrel, a drive mechanism for driving the pusher device, at least one coupling mechanism operative to couple the plunger to the pusher device or to couple the pusher device to the drive mechanism, and an actuation mechanism arranged on the pusher device and comprising an actuation element for actuating the at least one coupling mechanism between a coupling state and an uncoupling state, wherein the actuation mechanism comprises a first threaded element rotatable about a rotational axis and a second threaded element movable along the first threaded element, the second threaded element being in threaded engagement with the first threaded element and the first threaded element being operatively connected to the at least one coupling mechanism, the method comprising:

moving the actuation element to cause the second threaded element to move along the first threaded element, whereby moving the second threaded element along the first threaded element causes the first threaded element to rotate.

* * * * *